(12) United States Patent
Barrus et al.

(10) Patent No.: US 8,403,971 B2
(45) Date of Patent: Mar. 26, 2013

(54) POLYAXIAL SCREW ASSEMBLY

(75) Inventors: Michael Barrus, Ashburn, VA (US); Scott Jones, Mcmurray, PA (US)

(73) Assignee: K2M, Inc., Leesburg, VA (US)

( * ) Notice: Subject to any disclaimer, the term of this patent is extended or adjusted under 35 U.S.C. 154(b) by 138 days.

(21) Appl. No.: 12/739,506

(22) PCT Filed: Oct. 22, 2008

(86) PCT No.: PCT/US2008/080668
§ 371 (c)(1),
(2), (4) Date: Apr. 23, 2010

(87) PCT Pub. No.: WO2009/055400
PCT Pub. Date: Apr. 30, 2009

(65) Prior Publication Data
US 2011/0208248 A1   Aug. 25, 2011

Related U.S. Application Data

(60) Provisional application No. 61/000,072, filed on Oct. 23, 2007.

(51) Int. Cl.
*A61B 17/86* (2006.01)
*A61B 17/70* (2006.01)

(52) U.S. Cl. ........ 606/308; 606/305; 606/328; 606/266; 606/267; 606/269; 606/270; 403/322.2

(58) Field of Classification Search .......... 606/266–270, 606/305–308, 319, 328; 403/322.2
See application file for complete search history.

(56) References Cited

U.S. PATENT DOCUMENTS

| 5,676,666 | A | 10/1997 | Oxland et al. | |
|---|---|---|---|---|
| 5,733,286 | A | 3/1998 | Errico et al. | |
| 6,331,179 | B1 | 12/2001 | Freid et al. | |
| 6,554,834 | B1* | 4/2003 | Crozet et al. | 606/65 |
| 6,716,214 | B1 | 4/2004 | Jackson | |
| 6,881,215 | B2 | 4/2005 | Assaker et al. | |
| 6,893,444 | B2 | 5/2005 | Orbay | |
| 7,527,640 | B2 | 5/2009 | Ziolo et al. | |
| 7,922,748 | B2* | 4/2011 | Hoffman | 606/267 |
| 2004/0097933 | A1 | 5/2004 | Lourdel et al. | |

(Continued)

FOREIGN PATENT DOCUMENTS

EP    1090595 B1    12/2003

OTHER PUBLICATIONS

International Search Report of PCT/US2008/080668 dated May 6, 2010.

(Continued)

*Primary Examiner* — Eduardo C Robert
*Assistant Examiner* — Julianna N Harvey
(74) *Attorney, Agent, or Firm* — Carter, DeLuca, Farrell & Schmidt, LLP

(57) ABSTRACT

A polyaxial screw assembly includes a pedicle screw, a coupling, an insert, and a housing. The pedicle screw includes a shank having a helical thread formed thereon and a head at one end. The coupling is positioned on top the pedicle screw and releasably engages portions of the head. The coupling and pedicle screw are positioned within a distal portion of the housing. The pedicle screw is slid through an opening in the insert and the insert is thread into the distal portion of the housing to retain the coupling and the pedicle screw within the housing. The pedicle screw is rotatable and pivotable relative to the housing. Compressing the coupling within the housing locks the pedicle screw in a desired orientation.

9 Claims, 6 Drawing Sheets

U.S. PATENT DOCUMENTS

2004/0138662 A1* 7/2004 Landry et al. .................. 606/61
2005/0154391 A1* 7/2005 Doherty et al. ................ 606/61
2005/0192571 A1* 9/2005 Abdelgany ..................... 606/61
2006/0247631 A1 11/2006 Ahn et al.

OTHER PUBLICATIONS

Supplemental European Search Report for European Application No. 08841872 dated Jul. 2, 2012.

* cited by examiner

POLYAXIAL SCREW ASSEMBLY

CROSS-REFERENCE TO RELATED APPLICATIONS

The present application is a national stage application of International Application No. PCT/US2008/080668, published as WO2009/055400, filed Oct. 22, 2008, which claims priority to, and the benefit of, U.S. Provisional Patent Application Ser. No. 61/000,072, filed on Oct. 23, 2007, the entire contents of each of these prior applications which are hereby incorporated by reference herein.

BACKGROUND

1. Technical Field

The present disclosure relates to pedicle screws and, more particularly, to a polyaxial screw assembly.

2. Background of Related Art

The adult human spinal column has more than twenty discrete bones sequentially coupled to one another by a tri joint complex consisting of an anterior disc and the two posterior facet joints. The anterior discs of adjacent bones are cushioned by cartilage spacers referred to as intervertebral discs. The bones of the spinal column are anatomically categorized as being members of one of four classifications: cervical, thoracic, lumbar, or sacral. The cervical portion of the spine is the top of the spine and includes the first seven vertebrae from the base of the skull. The next twelve bones are the thoracic vertebrae. Thereafter, the next five bones form the lumbar vertebrae. Connecting to the lumbar, the sacral bones are at the base of the spine and include the coccyx.

The spine is a highly flexible structure, capable of a high degree of curvature and twist in nearly every direction. Genetic or developmental irregularities, trauma, chronic stress, tumors, and disease, however, can result in spinal pathologies. Spinal pathologies either limit the range of motion of the spine or threaten the critical elements of the nervous system housed within the spinal column. There are many systems that immobilize the spine by implanting artificial assemblies in or on the spinal column. The implantable assemblies are classified as anterior, posterior, or lateral implants. As the name of the classification suggests, lateral and anterior implants are coupled to the anterior portion of the spine. Posterior implants generally comprise rod assemblies that are attached to the spinal column by either 1) hooks coupled to the lamina or the transverse processes, or 2) by screws inserted through the pedicles.

The screws are implanted through the posterior lateral surfaces of the laminae, through the pedicles, and into their respective vertebral bodies. The screws have upper portions that are coupling elements for receiving and securing an elongate rod. The elongate rod extends along the axis of the spine and is coupled to the screws via the coupling elements. The rigidity of the elongated rod aligns the spine in a more desired shape.

Inserting screws along a misaligned curvature of the spine, while exactly positioning the coupling elements, can be difficult. The coupling elements must be placed in a way that a rod can be passed therethrough without damaging the screws. As a result, the surgeon must be careful when trying to properly align fixed screws, which increases the operating time and leads to an increased probability of a complication.

The art contains screws that permit a limited amount of freedom with respect to angulation of the coupling element. These assemblies, however, are generally complex, unreliable, and lack durability.

SUMMARY

A polyaxial screw assembly is presently disclosed. The polyaxial screw assembly includes a pedicle screw, a coupling, a housing, and an insert. The pedicle screw has a head having a recess and a plurality of gaps. The coupling has a plurality of knobs that mate with the plurality of gaps and the lower surface of the coupling mates with the recess in the head of the pedicle screw. The housing has a passageway that forms a longitudinal axis through the housing. The passageway narrows at a point between a distal opening and a proximal opening. The distal portion of the passageway is partially threaded. The insert is configured to be slid over the shank of the pedicle screw and thread into the distal opening of the housing. The insert has a threaded outer diameter that mates with the threaded distal portion of the housing and an opening extending therethrough. The diameter of the opening of the insert is dimensioned to be less than the outer diameter of the head and greater than the shank of the pedicle screw. As a result, the insert sandwiches the pedicle screw and coupling within the housing.

Threading the insert into the bottom of the housing joins the pedicle screw and coupling arrangement to the housing, thereby forming the polyaxial screw assembly. As assembled, the pedicle screw is rotatable and pivotable in the housing.

A proximal portion of the housing is shaped to form a U-shaped saddle. Placing a rod member in the saddle of the housing acts to compress the head of the pedicle screw against an inner surface of the housing, thereby securing the pedicle screw in a desired orientation. A locking member or setscrew is then threaded into the top of the housing for securing the rod member in position with respect to the housing. Each part of the polyaxial screw assembly is made of a biocompatible material.

BRIEF DESCRIPTION OF THE DRAWINGS

Embodiments of the presently disclosed polyaxial screw assembly are described herein with reference to the accompanying drawings, wherein.

Figure 1A:
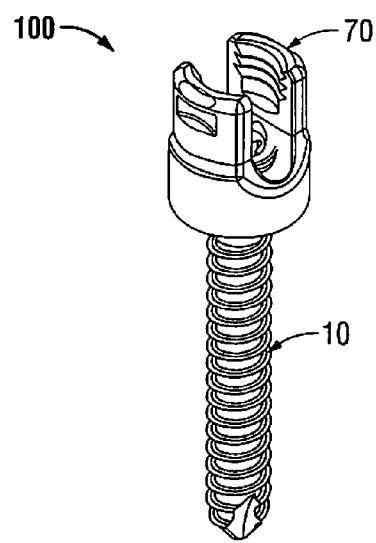
FIG. 1A is a perspective view of a polyaxial screw assembly according to the present disclosure.

Other features and advantages of the present disclosure will become apparent from the following detailed description, taken in conjunction with the accompanying drawings, which illustrate, by way of example, the principles of the present disclosure.

DETAILED DESCRIPTION OF THE EMBODIMENTS

Embodiments of the presently disclosed polyaxial screw assembly will now be described in detail with reference to the drawing figures wherein like reference numerals identify similar or identical elements. In the drawings and in the description which follows, the term "proximal", as is traditional, will refer to the end of the polyaxial screw assembly which is closest to the operator while the term "distal" will refer to the end of the polyaxial screw assembly which is furthest from the operator.

Figure 1B:
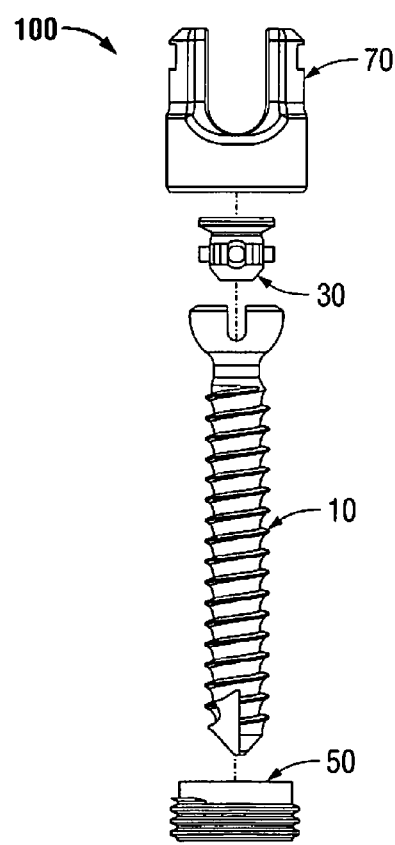
FIG. 1B is an exploded front view, with parts separated, of the polyaxial screw assembly of FIG. 1A.

Referring initially to FIGS. 1A and 1B, in which like reference numerals identify similar or identical elements, a polyaxial screw assembly is generally designated as 100. The polyaxial screw assembly 100 includes a pedicle screw 10, a coupling 30, an insert 50, and a housing 70. The steps of assembling the polyaxial screw assembly 100 include positioning the coupling 30 on top of the pedicle screw 10 and then the housing 70 is positioned over the coupling 30 and the pedicle screw. Then the insert 50 is passed over the distal end of the pedicle screw 10 and along the shaft towards the bottom of the housing 70. The insert 50 is then screwed into the housing 70 to hold the polyaxial screw assembly 100 together. The specific arrangements and interconnections of the various components will be described in further detail hereinafter.

Figure 2A:
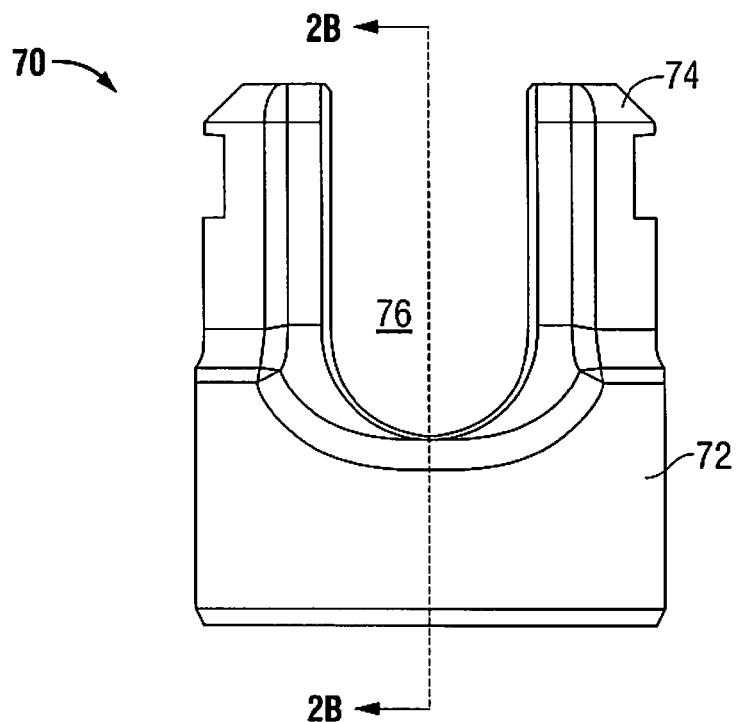
FIG. 2A is a side cross-sectional view, taken along section line A-A, of the housing of FIG. 2.
Figure 2B:
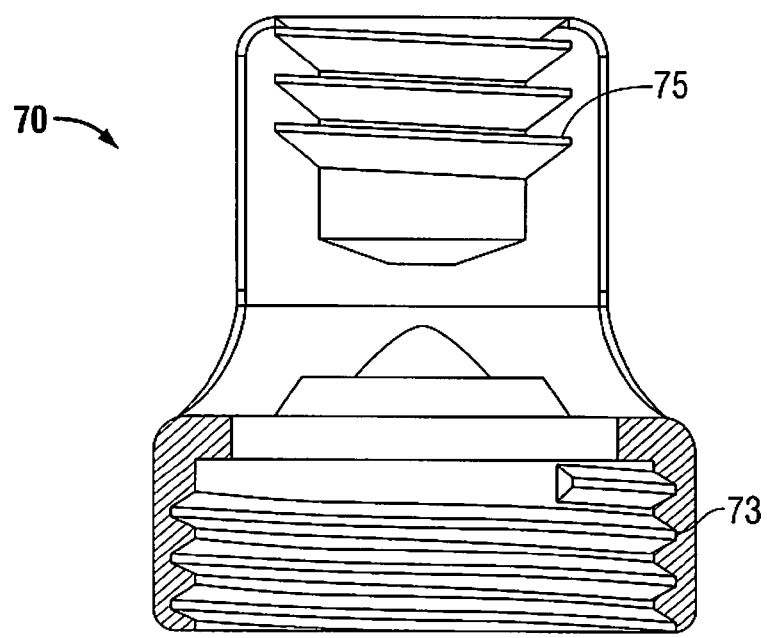
FIG. 2 is a front view of a housing.

Turning now to FIGS. 2 and 2A, the housing 70 will be described in additional detail. The housing 70 includes an annular body portion 72 having an opening therethrough with a pair of upstanding fingers 74. A U-shaped saddle 76 is defined between the fingers 74 and is configured for receiving a rod member (not shown). The body portion includes a generally helical thread 73 that is located in a lower section of the body portion 72 and is adapted for threadably engaging a corresponding thread 56 of the insert 50, as will be described in detail hereinafter. Each of the fingers 74 includes a portion of a generally helical thread 75 formed on the inner surface of the housing. The thread 75 is configured for threadably engaging a corresponding thread on a locking element (not shown). The locking element may be a setscrew or another threaded component, as is known in the art. The opening at the bottom of the housing 70 is capable of receiving the coupling 30 and the pedicle screw 10 without being able to completely pass therethrough.

Figure 4:
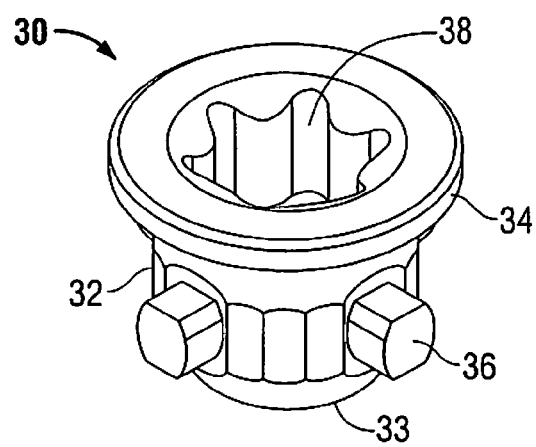
FIG. 4 is a perspective view of a coupling.

As seen in FIG. 4, the coupling 30 has a generally annular body 32 with a plurality of outwardly extending knobs 36. In the illustrated embodiment, four knobs 36 are shown and each knob 36 is offset 90° from the adjacent knobs 36. It is envisioned that the knobs extend from the screw head and the annular body of the coupling has recesses to accept the knobs. An annular flange 34 is disposed at one end of the coupling 30. The flange 34 has an outer diameter that is greater than the outer diameter of the body 32. Additionally, a recess 38 is formed in the body 32 of the coupling 30. The recess 38 is configured and adapted for releasable engagement with a driving tool (not shown), as is known in the art. Although the recess 38 is illustrated with a six-pointed star pattern, other suitable configurations are contemplated. A tapered outer surface 33 is located about the distal end of the coupling 30.

Figure 5:
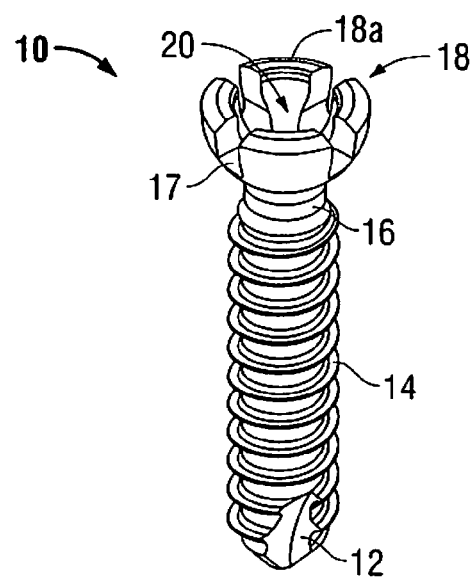
FIG. 5 is a perspective view of a pedicle screw.

Turning now to FIG. 5, the pedicle screw 10 will be discussed in detail. The pedicle screw 10 includes a shank 16 having a helical thread 14 formed thereon. A cutting portion 12 is formed at a distal end of the pedicle screw 10. A head 18 is located at a proximal end of the pedicle screw 10 and includes a plurality of segments 18a. The segments 18a are arranged in a circular configuration about the head 18. A gap 17 exists between each of the segments 18a and is adapted for releasably receiving the plurality of knobs 36 of the coupling 30 (FIG. 4). A recess 20 is defined between the segments 18a in the center of the head 18. The recess 20 has a tapered inner surface for receiving the body 32 of the coupling 30 (FIG. 4).

When the coupling 30 is located in the recess 20, each of the knobs 36 are positioned within one of the corresponding gaps 17. Thus, the coupling 30 and the pedicle screw 10 are rotatably coupled such that rotation of the coupling 30 causes a corresponding rotation of the pedicle screw 10.

Figure 3:
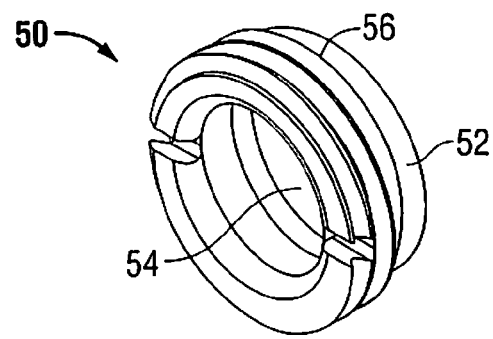
FIG. 3 is a bottom perspective view of an insert.

As seen in FIG. 3, the insert 50 is an annular ring 52 having an opening 54 extending therethrough. The opening 54 has a diameter that is greater than the shank 16 of the pedicle screw 10 and is smaller than the head 18 of the pedicle screw 10. A generally helical thread 56 is located on the outer surface of the annular ring 52. The thread 56 mates with the thread 75 of the housing 70 (see FIG. 2A).

Referring to FIGS. 1A-5, assembly and usage of the polyaxial screw assembly 100 will now be discussed in detail. Initially, the coupling 30 is seated within the top of the pedicle screw 10, such that each of the knobs 36 is interlocked with a corresponding gap 17 and the outer diameter of the coupling body 32 pivotably mates with the inner diameter of the pedicle screw recess 20. As a result, the coupling 30 is slidably received in the recess 20. The tapered outer surface 33 mates with the tapered inner surface of the recess 20 and allows the coupling 30 to be seated within the recess 20.

As previously discussed, when the coupling 30 is seated in the recess 20 of the pedicle screw 10, rotation of the coupling 30 causes a corresponding rotation of the pedicle screw 10, thereby allowing the pedicle screw 10 to be inserted and removed from a target location. The interaction of coupling 30 and recess 20 in screw 10 permits the screw to be driven in response to a driver tool which engages the coupling, even if the screw is disposed at an angle relative to the coupling. Thus, the screw shaft and driving tool can be out of alignment during insertion of the screw into bone.

The coupling 30 and the pedicle screw 10 are inserted into the housing 70. The distal opening in the housing 70 has a greater diameter than the outer diameters of either the head 18 or the coupling 30. The insert 50 is slid over the shank 16 of the pedicle screw 10 and threaded into the bottom of the housing 70. The opening 54 of the insert 50 has a diameter that is less than that of the head 18 of the pedicle screw 10, thereby inhibiting the pedicle screw 10 from passing through the opening 54 of the insert 50. By threading the insert 50 into the bottom of the housing 70, the pedicle screw 10 and the coupling 30 are retained in the housing and form the assembled polyaxial screw assembly 100. The pedicle screw 10 is rotatable and pivotable in relation to the housing 70.

After the polyaxial screw assembly 100 is positioned at a desired location in a patient, a rod member (not shown) is placed in the saddle 76 and is retained in the housing 70 using a locking screw (not shown). As the locking screw is tightened against the rod member, the rod member presses against the coupling 30, thereby pressing the head 18 of the pedicle screw 10 against the inner surfaces of the insert 50 and securing the pedicle screw 10 in position (i.e. locks the screw in place).

Polyaxial screw assembly 100 may be composed of a range of biocompatible materials including, but not limited to, titanium, titanium alloys, stainless steel, cobalt chrome and cobalt chrome alloys, ultra high molecular weight polyethylene, PEEK (polyetheretherketone), and other polymers such as polycarbonate urethane. A variety of manufacturing techniques may be employed to produce polyaxial screw assembly 100.

Figure 6:
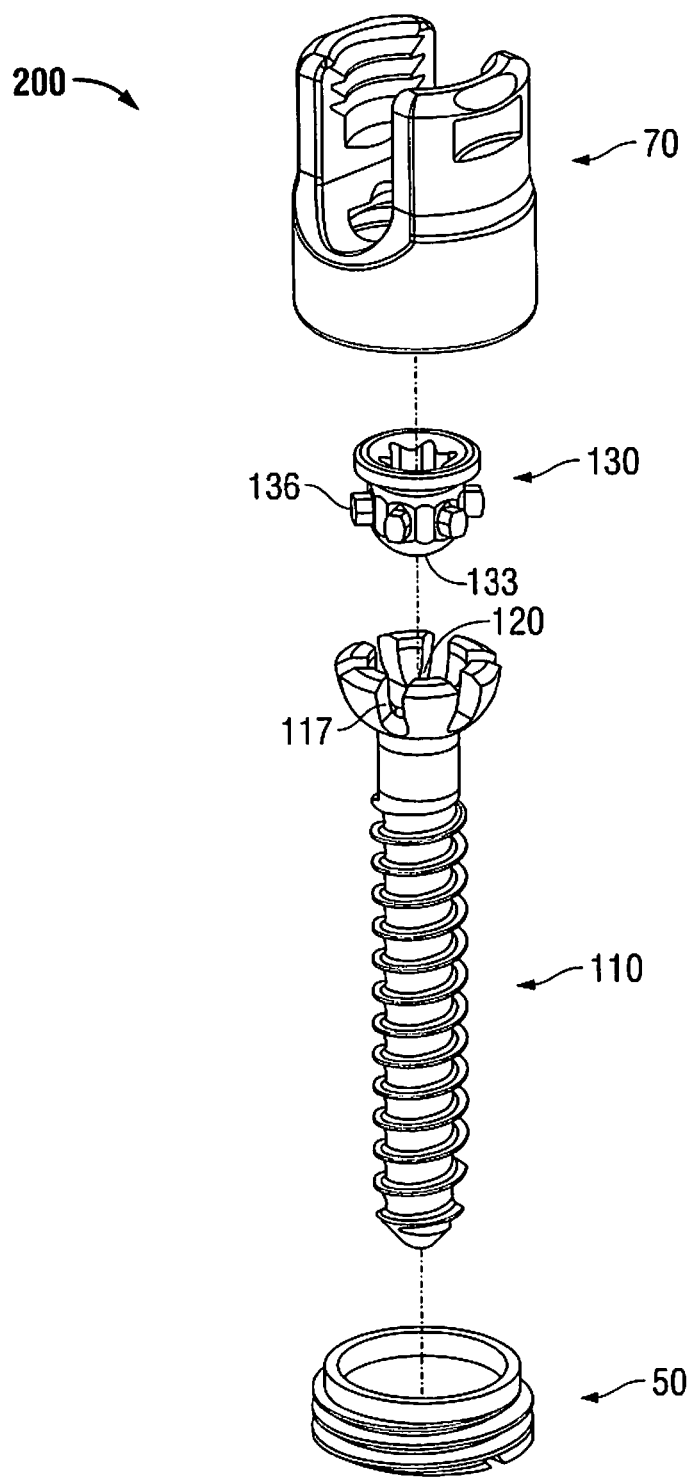
FIG. 6 is an exploded front view, with parts separated, of a polyaxial screw assembly in accordance with another embodiment of the present disclosure.

In another embodiment, shown in FIG. 6, polyaxial screw assembly 200 includes a pedical screw 110, a coupling 130, an insert 50, and a housing 70. The insert 50 and the housing 70 are similar to those of polyaxial screw assembly 100. Pedicle screw 110 is similar to pedicle screw 10, except that pedicle screw 110 has six gaps 117 placed an equal distance about a recess 120. Coupling 130 is similar to coupling 30, except that coupling 130 has six knobs 136 placed an equal distance about the tapered outer surface 133. The six knobs 136 of the coupling 130 align with the six slots 117 of the pedicle screw 110. The tapered outer surface 133 and recess 120 slidably interface. It is envisioned that other numbers of knobs and slots may be utilized.

Figure 7:
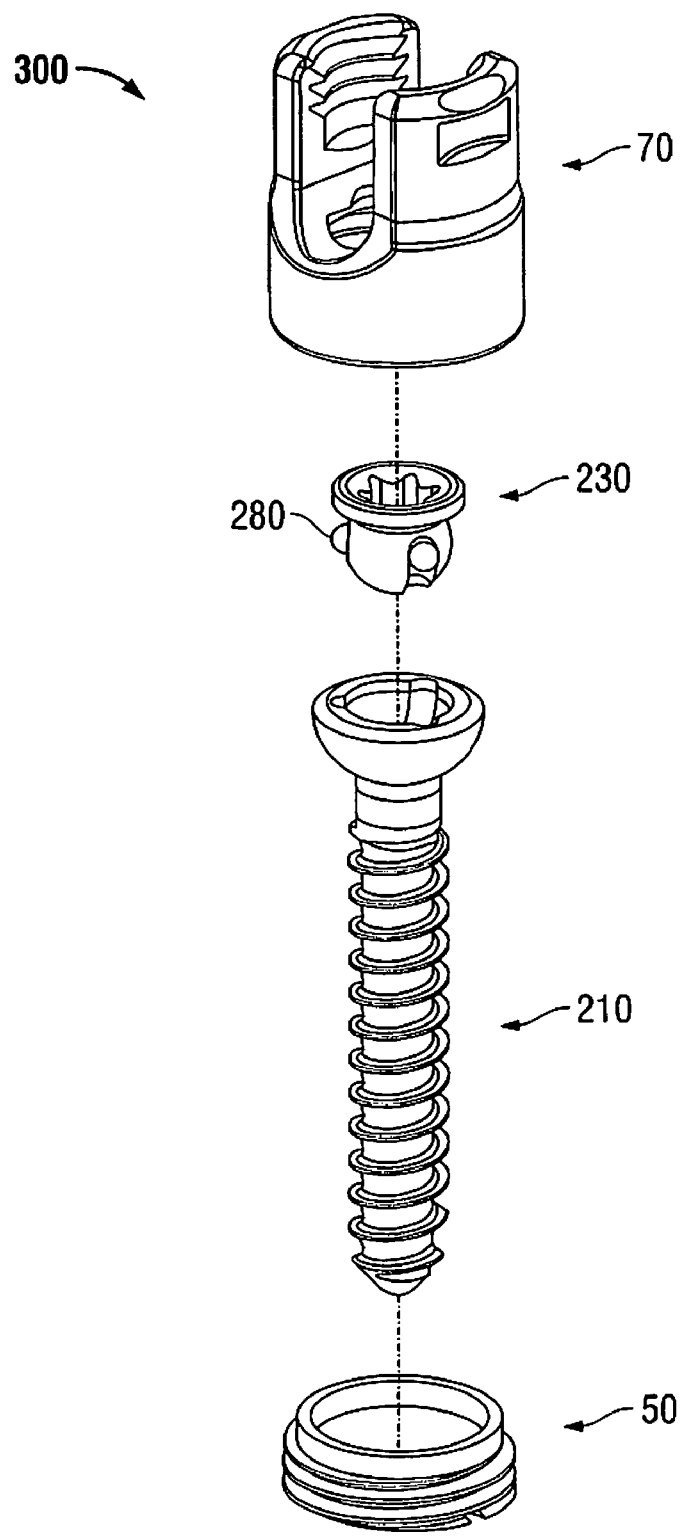
FIG. 7 is an exploded front view, with parts separated, of a polyaxial screw assembly in accordance with still another embodiment of the present disclosure.
Figure 8:
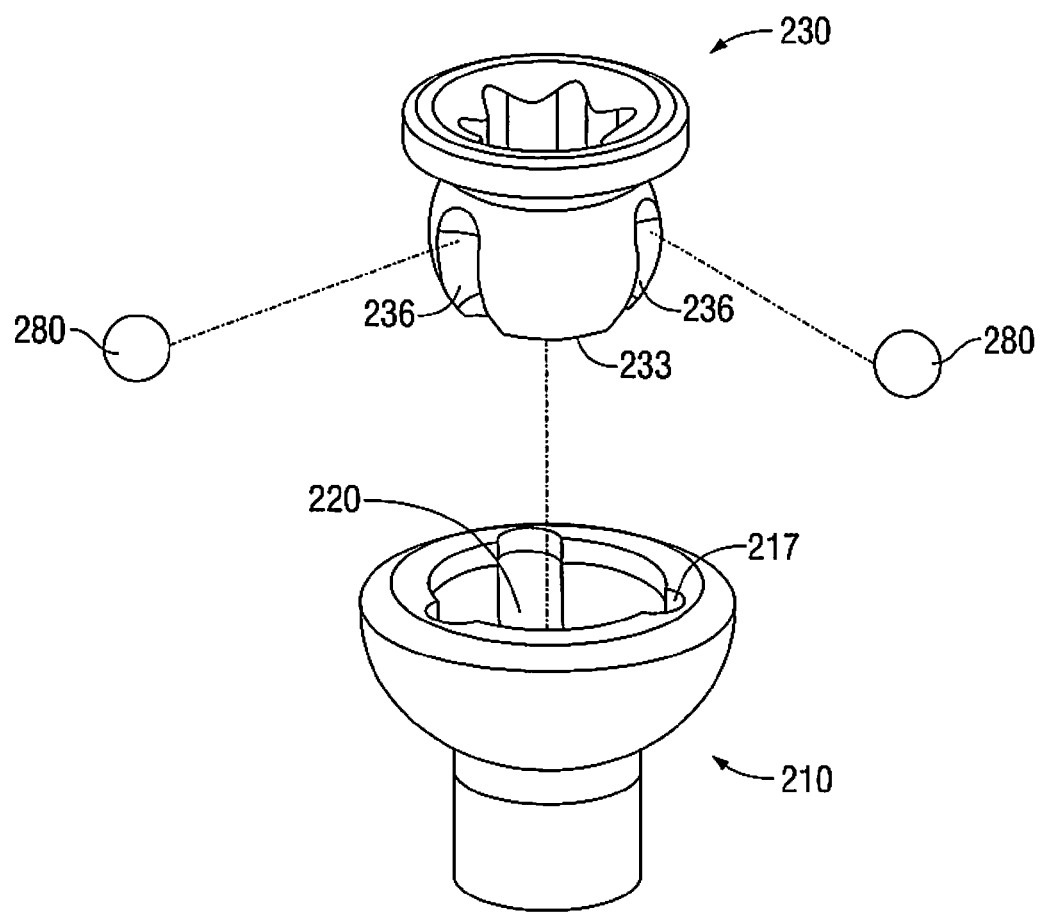
FIG. 8 is a perspective view of the coupling, the pedicle screw, and three connectors in accordance with the embodiment of FIG. 7.

In still another embodiment, shown in FIGS. 7 and 8, polyaxial screw assembly 300 includes a pedicle screw 210, a coupling 230, an insert 50, a housing 70, and three connectors 280. The insert 50 and the housing 70 are similar to those of polyaxial screw assembly 100. Pedicle screw 210 is similar to pedicle screw 10, except that pedicle screw 210 does not have gaps 17. Pedicle screw 210 has three slots 217 placed an equal distance about a recess 220. Coupling 230 is similar to coupling 30, except that coupling 230 does not have knobs 36. Coupling 230 has three slots 236 placed an equal distance about the tapered outer surface 233. The slots 236 of the coupling 230 match with slots 217 of the pedicle screw. As shown in FIG. 8, three generally spherical load transferring connectors 280 are sized to fit into slots 217 and slots 236. The tapered outer surface 233 and recess 220 are allowed to slidably interface.

It will be understood that various modifications may be made to the embodiments of the presently disclosed polyaxial screw assembly. By way of example only, the insert could be welded to the housing instead of or in addition to engaging the housing by a threaded engagement. Therefore, the above description should not be construed as limiting, but merely as exemplifications of embodiments. Those skilled in the art will envision other modifications within the scope and spirit of the present disclosure.

What is claimed is:

1. A polyaxial screw assembly comprising:
   a screw having a shank and a head, the head having a concave recess and defining at least one slot within an interior surface of the concave recess;
   a coupling configured to be received within the concave recess of the screw head, the coupling defining at least one slot within an outer surface thereof;
   at least one spherical member slidably received within the at least one slot of the head of the screw and the at least one slot of the coupling;
   a housing having a passage therethrough for receiving the screw head and the coupling; and
   an insert having an opening therethrough to receive the screw shank, the insert being engageable with the housing to retain the screw head and the coupling in the housing.

2. The polyaxial screw assembly according to claim 1, wherein rotational force applied to the coupling is translated through the at least one spherical member to cause rotation of the screw.

3. The polyaxial screw assembly according to claim 2, wherein the coupling and the screw are disposed at an angle to each other as the rotational force is applied.

4. The polyaxial screw assembly according to claim 1 wherein the housing passage includes a threaded portion and the insert has threads on an exterior surface thereof, the threads of the insert engageable with the threads of the housing passage to retain the screw head and the coupling in the housing.

5. The polyaxial screw assembly according to claim 1, wherein the coupling defines a plurality of equally-spaced slots.

6. The polyaxial screw assembly according to claim 1, wherein the screw defines a plurality of equally-spaced slots.

7. A polyaxial screw assembly comprising:
   a screw having a shank and a head, the head having a concave recess and defining at least one slot within an interior surface of the concave recess;
   a coupling configured to be received within the concave recess of the screw head, the coupling defining at least one slot within an outer surface thereof;
   at least one spherical member slidably received within the at least one slot of the screw head and the at least one slot of the coupling; and
   a housing having a passage therethrough for receiving the screw head and the coupling.

8. The polyaxial screw assembly according to claim 7, further comprising an insert engageable with the housing to retain the screw head and the coupling in the housing.

9. The polyaxial screw assembly according to claim 7, wherein rotational force applied to the coupling is translated through the at least one spherical member to cause rotation of the screw.

* * * * *